(12) United States Patent
Ebersole et al.

(10) Patent No.: US 7,790,876 B2
(45) Date of Patent: Sep. 7, 2010

(54) SEQUENCES DIAGNOSTIC FOR FOOT AND MOUTH DISEASE

(75) Inventors: Richard C. Ebersole, Wilmington, DE (US); Linda J. DeCarolis, Newark, DE (US); Raymond E. Jackson, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 391 days.

(21) Appl. No.: 10/538,590

(22) PCT Filed: Dec. 19, 2003

(86) PCT No.: PCT/US03/41808
§ 371 (c)(1),
(2), (4) Date: Jul. 30, 2007

(87) PCT Pub. No.: WO2004/058300
PCT Pub. Date: Jul. 15, 2004

(65) Prior Publication Data
US 2008/0032285 A1 Feb. 7, 2008

Related U.S. Application Data

(60) Provisional application No. 60/434,974, filed on Dec. 20, 2002.

(51) Int. Cl.
*C07H 21/04* (2006.01)
*A61K 39/135* (2006.01)
(52) U.S. Cl. .................. 536/24.33; 424/216.1
(58) Field of Classification Search ........................ None
See application file for complete search history.

(56) References Cited

U.S. PATENT DOCUMENTS

| 5,639,601 A | 6/1997 | Saeki et al. |
| 6,048,538 A | 4/2000 | Wang et al. |
| 2003/0149259 A1* | 8/2003 | Callahan et al. .......... 536/24.32 |

FOREIGN PATENT DOCUMENTS

WO      WO 02/095074 A1      11/2002

OTHER PUBLICATIONS

D. Adam et al., More Culls Planned as Britain Wrestles With Foot-and-Mouth, Nature, 2001, vol. 410:398.
M. Enserink, Barricading U.S. Borders Against a Devastating Disease, Science, 2001, vol. 291:2298-2300.
Gilles et al., A Solid-Phase Blocking Elisa for Detection of Type O Foot-and-Mouth Disease Virus Antibodies Suitable for Mass Serology, J. Virological Methods, 2003, vol. 107:89-98.
MacKay et al., A Solid-Phase Competition Elisa for Measuring Antibody to Foot-and-Mouth Disease Virus, J. Virological Methods, 2001, vol. 97:33-48.
Bergmann et al., Improvement of a Serodiagnostic Strategy for Foot-and-Mouth Disease Virus Surveillance in Cattle Under Systematic Vaccination: A Combined System of an Indirect Elisa-3ABC With an Enzyme-Linked Immunoelectrotransfer Blot Assay, Archives of Virology, 2000, vol. 145:473-489.
N.P. Ferris, Proceedings of an International Symposium on Diagnosis and Control of Livestock Diseases Using Nuclear and Related Techniques, Vienna, 1998, pp. 65-77, International Atomic Energy Agency.
Collins et al., A Method to Detect Major Serotypes of Foot-and-Mouth Disease Virus, Biochemical and Biophysical Research Communications, 2002, vol. 297:267-274.
Reid et al., Detection of All Seven Serotypes of Foot-and-Mouth Disease Virus by Real-Time Fluorogenic Reverse Transcription Polymerase Chain Reactions Assay, J. Virological Methods, 2002, vol. 105:67-80.
Callahan et al., Use of a Portable Real-Time Reverse Transcriptase Polymerase Chain Reaction Assay for Rapid Detection of Foot-and-Mouth Disease Virus, J. American Veterinary Medical Association, 2002, vol. 220:1636-1642.
Pattnaik et al., Evaluation of Primers for PCR Amplification of RNA Polymerase Gene Sequences of Foot-and-Mouth Disease Virus, 1997, vol. 41:333-336.
Baranowski et al., Multiple Virulence Determinants of Foot and Mouth Disease Virus in Cell Culture, Journal of Virology, 1998, vol. 72:6362-6372.
M. Hofmann et al., Rescue of Infectious Classical Swine Fever and Foot-and-Mouth Disease Virus by RNA Transfection and Virus Detection by RT-PCR After Extended Storage of Samples in Trizol, Journal of Virological Methods, 2000, vol. 87:29-390.
Beard,C.W. and Mason,P.W, Genbank Accession No. AF308157, Foot-and-mouth disease virus, complete genome (2000).
Beard,C.W. and Mason,P.W, .Genetic determinants of altered virulence of Taiwanese foot-and-mouth disease virus, J. Virol. 74 (2), 987-991 (2000).

* cited by examiner

*Primary Examiner*—Stacy B Chen

(57) ABSTRACT

Methods and materials for the detection of the foot and mouth disease virus (FMDV). The methods may utilize PCR amplification, with or without an internal positive control, and appropriate primer pairs. The reagents to perform these methods can be supplied as a kit and/or in tablet form.

8 Claims, 6 Drawing Sheets

Figure 1

Not1 Site

5' gcggccgcgccccggccactttggccattcacccgagcgaagctagacacaaacaaaagatt
gtggcaccggtgaaacagctttgacctgctcaagttggcagggacgtcgagtccaaccct
gggcctttctctctgacgttagtcaaatttttccaagtggttgaaccatcaaccagatgcaggag
gacatgtcaacaaacacggaccgacttaaccggttgtctgcatttgaggaactggccaccgg
agtgaaggctatcaggacctgtcgatgaggccaaacctggtacaagctcatcaagctcttgagc
cgcctgtcatgtatggccgtgctgtagcagcggtcaaagaccagtccttgtggccatcatgctggct
gacaccggccttgagattctggacagtacccttgtcgtgaagaagatctccgactgctcgctctcttt
cacgtaccggcccccgtcttcagtttcggggaattc 3'

EcoRI site

(SEQ ID NO:21)

P33-4
224bp

LJS1
550bp

LJS2
400bp

Figure 6
Mechanism of melting curve analysis
Data Transformation
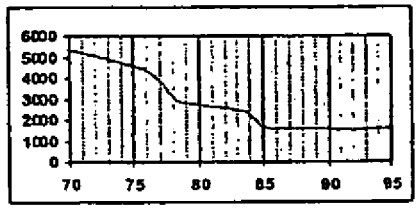
Raw Data
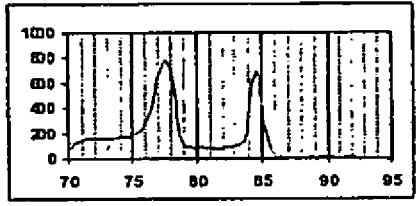
Processed Data
Data transformations involve the following:
1. Interpolate data to get evenly spaced data points
2. Take log of fluorescence (F)
3. Smooth log F
4. Calculate $-d(\log F)/dT$    $-d_F/d_T$
5. Reduce data to 11-13 data points spaced one degree apart depending on the target organism

SEQUENCES DIAGNOSTIC FOR FOOT AND MOUTH DISEASE

This application represents a national filing under 35 USC 371 of International Application No. PCT/US03/41808 filed Dec. 19, 2003 and claims the benefit of U.S. Provisional Application No. 60/434,974, filed Dec. 20, 2002, the entire contents of which is hereby incorporated by reference in its entirety.

FIELD OF THE INVENTION

The field of invention relates to diagnostic testing, and more specifically, to diagnostic methods and materials for detecting the Foot and Mouth Disease Virus (FMDV).

BACKGROUND OF THE INVENTION

Recent events in the United Kingdom have demonstrated very clearly that foot and mouth disease virus (FMDV) is so highly contagious that rapid diagnosis is required to control its spread. See, e.g., Adam, D., *Nature* 410:398 (2001) and Enserink, M., *Science* 291:2298-2300 (2001).

Foot and Mouth Disease Virus (FMDV) is actually a group of closely related viruses, classified as members of the genus *Aphthovirus* and family Picornaviridae. The genus *Aphthovirus* has two members, FMDV and Equine Rhinitis A Virus (ERV-1). The second genus member, ERV-1, shares some sequence homology with FMDV, but is not a cause of foot and mouth disease (FMD). ERV-1 is the agent of an equine respiratory disease (horses are not susceptible to FMDV).

There are seven serotypes of FMDV: types A, O, C, Asia 1, Sat 1 (South African Territories), Sat 2, and Sat 3. Serotypes are distinguishable by serotype-specific enzyme linked immunosorbent assays (ELISA).

Because of the range of species affected, the high rate of infectivity, and the fact that FMDV is shed before clinical signs occur, FMD is one of the most feared reportable diseases known in North America. Disease caused by FMDV is devastating to farm animals and can have a major economic impact on countries producing cloven-hoofed animals (cattle, pigs, sheep, goats and camelids) or their products. Clearly, new and more sensitive assays for the detection of this disease are needed.

A variety of methods for the detection of FMDV have been developed. These fall into three general categories: 1) detection of FMDV peptides; 2) detection of FMDV generated antibodies; and 3) detection of FMDV genetic material.

A number of peptides have been identified that are unique to the FMDV and are considered diagnostic for its presence. These include both structural proteins as well as non-structural proteins (see, e.g., Yi et al., U.S. Pat. No. 6,048,538; Saeki et al., U.S. Pat. No. 5,639,601).

In other cases methods have been developed to detect antibodies generated by the infected animal to the FMDV. The ELISA assay is a preferred format (see, e.g., Gilles et al., *J. Virological Methods* 107(1):89-98 (2003); Mackay et al., *J. Virological Methods* 97(1-2):33-48 (2001); Bergmann et al., *Archives of Virology* 145(3):473-489 (2000); and Ferris, N. P., Towards Livestock Disease Diagnosis and Control in the 21st Century, Proceedings of an International Symposium on Diagnosis and Control of Livestock Diseases Using Nuclear and Related Techniques, Vienna, Apr. 7-11, 1997 (1998), Meeting Date 1997, 65-77, International Atomic Energy Agency, Vienna, Austria).

A common and effective method of assay has been the use of primer directed nucleic amplification methods for the amplification of diagnostic portions of the FMDV genome. These methods are based on the isolation of primers or probes that are particularly diagnostic for the presence of the virus. Collins et al. (*Biochemical and Biophysical Research Communications* 297(2):267-274 (2002)) teach an isothermal method of nucleic acid sequence-based amplification using primers based on a variety of loci in the FMDV genome. One of the most popular methods for detection is the use of a method involving reverse transcription followed by polymerase chain reaction (RT-PCR). As its name implies, the method involves the synthesis of DNA by reverse transcription and then the amplification of DNA by PCR. Callahan et al. (WO 02/095074) use this method for the detection of FMDV using primers derived from highly conserved regions of the 3D coding region of the genome. Reid et al. (*J. Virological Methods* 105(1):67-80 (2002)) teach a fluorogenic RT-PCR assay using a primer/probe set designed from the internal ribosomal entry site region of the virus genome that was capable of detecting all seven serotypes of the FMDV. The primer-based methods are amenable to a variety of formats and kits (see, e.g., Callahan et al., *J. American Veterinary Medical Association* 220(11): 1636-1642 (2002).

All of the above methods have been used in the detection of FMDV. However, tests with reliable breadth of specificity for "universal" detection of all strains and increased sensitivity, along with ease and reliability of use, are still needed in an FMDV assay. Additionally, because of the high gene mutation rate in the virus, tests directed to different regions of the genome would be useful. There is a need, therefore, for a highly sensitive assay for FMDV that broadly detects most strains of the virus, is rapid, accurate and easily performed.

SUMMARY OF THE INVENTION

A method for detecting the presence of FMDV in a sample, the method comprising performing RT-PCR amplification of the sample using at least one primer pair selected from the group consisting of SEQ ID NOs:16 and 17, SEQ ID NOs:16 and 18, SEQ ID NOs:16 and 19, and SEQ ID NOs:16 and 20, to produce an RT-PCR amplification result; and examining the RT-PCR amplification result to detect for an amplification product of the primer pair, whereby a positive detection of the amplification product indicates the presence of FMDV in the sample. Preferably, a melting curve analysis is used to detect for an amplification product. The method may also comprise a step of extracting RNA from the sample, preferably prior to the step of performing RT-PCR amplification of the sample.

An isolated polynucleotide for detection of FMDV comprising SEQ ID NO:16, SEQ ID NO:17, SEQ ID NO:18, SEQ ID NO:19, or SEQ ID NO:20.

A kit for detection of FMDV, comprising at least one primer pair selected from the group consisting essentially of SEQ ID NOs:16 and 17, SEQ ID NOs:16 and 18, SEQ ID NOs:16 and 19, and SEQ ID NOs:16 and 20; reverse transcriptase; and thermostable DNA polymerase.

A replication composition for use in performance of RT-PCR, comprising at least one primer pair selected from the group consisting essentially of SEQ ID NOs:16 and 17, SEQ ID NOs:16 and 18, SEQ ID NOs:16 and 19, and SEQ ID NOs:16 and 20; reverse transcriptase; and thermostable DNA polymerase. Preferably, a replication composition is in the form of a tablet, and a detection kit comprises a tablet replication composition of the present application.

BRIEF DESCRIPTION OF THE DRAWINGS AND SEQUENCE DESCRIPTIONS

FIG. 1 is the DNA sequence of a synthetic FMD target (SEQ ID NO:21)

Figure 3:
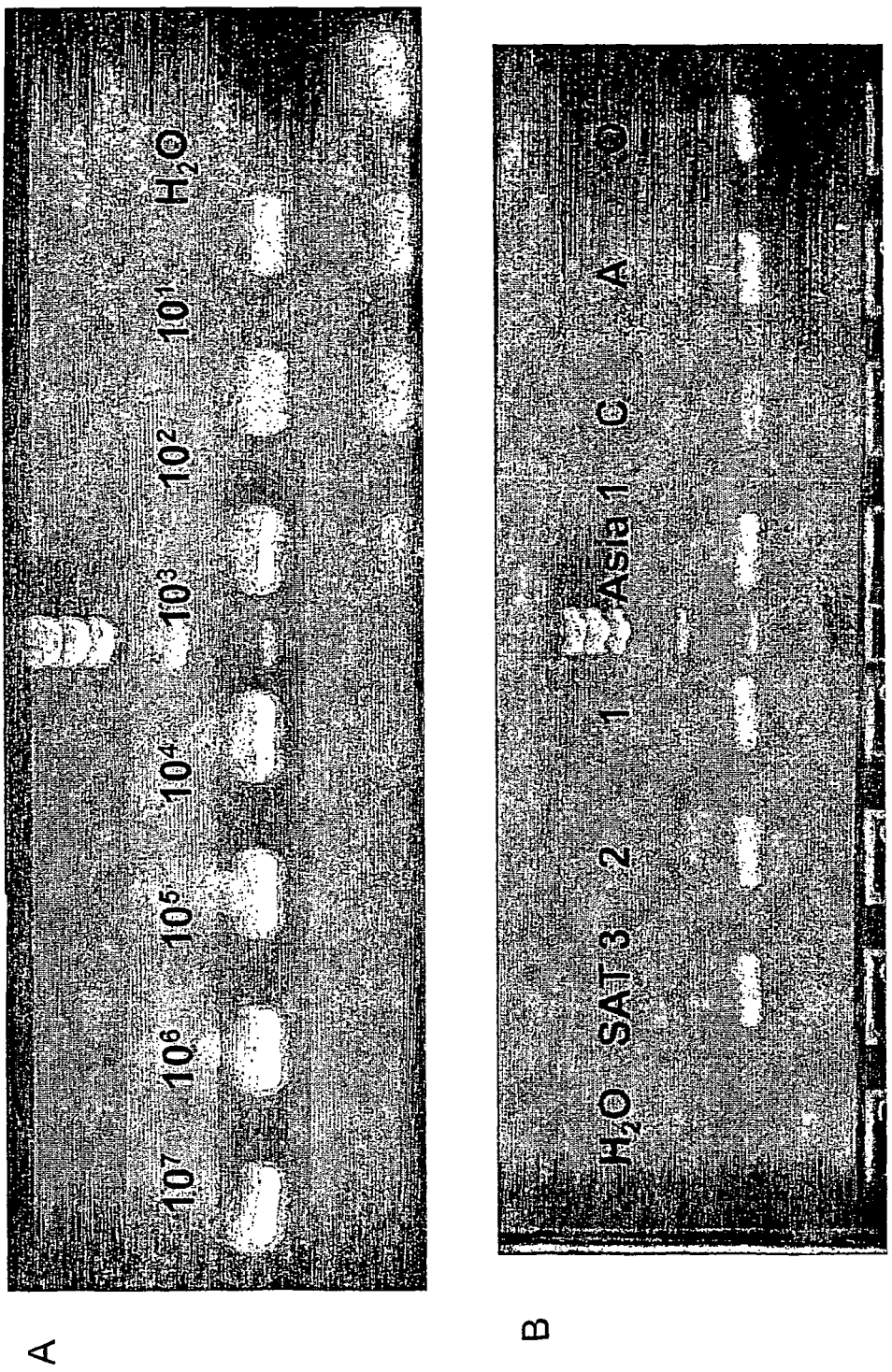

FIGS. 3A-3B show agarose gel electrophoresis results from RT-PCR reactions. Specifically, FIG. 3A shows RT-PCR amplification product obtained using primers P2Fwd-10 and P33-4 and using samples containing serial log dilutions of the synthetic FMD target RNA from $10^7$ copies to $10^1$ copies/test. FIG. 3B shows the RT-PCR amplification product using the P2Fwd-10 and P33-4 primers with a representative strain from each of the seven FMD viral serotypes at a starting viral RNA concentration of $10^2$ viral RNA-copies/test.

Figure 4:
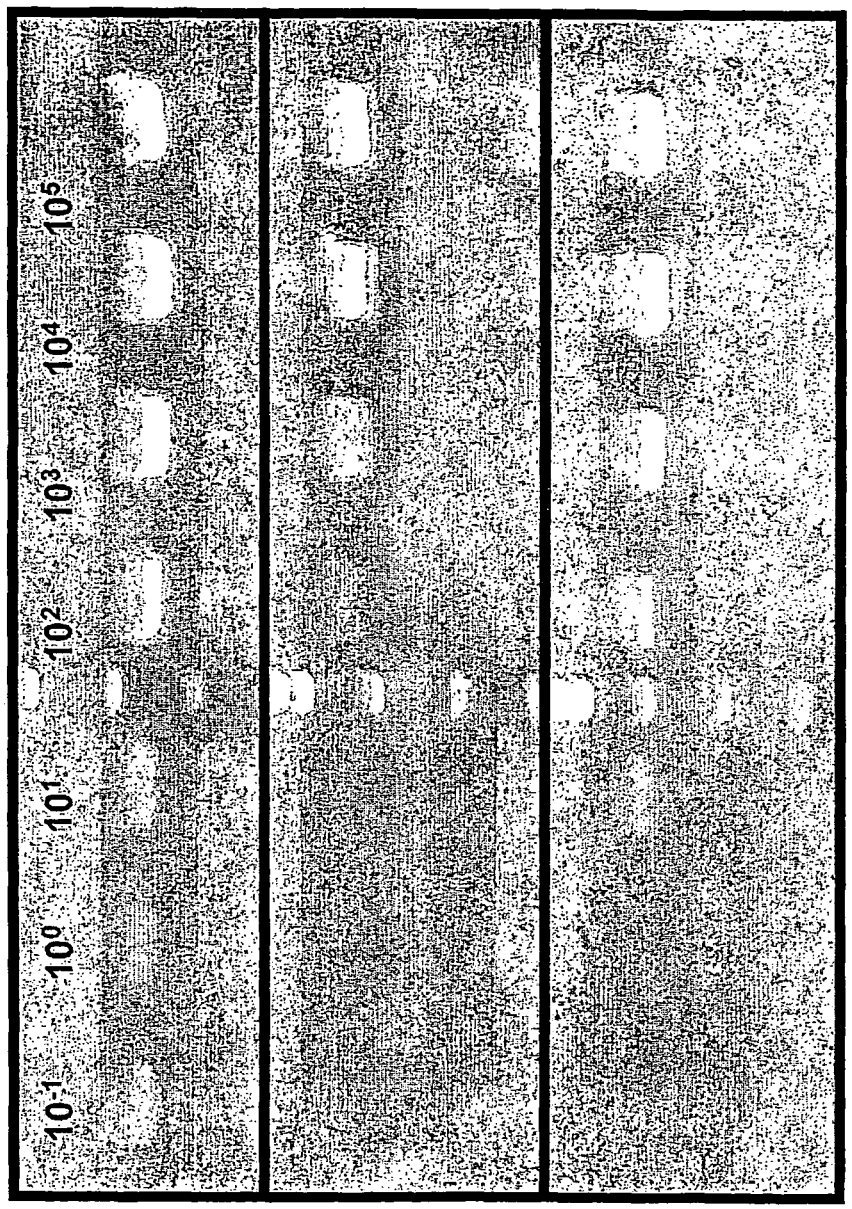

FIG. 4 is a composite picture of three agarose electrophoresis gels showing the RT-PCR amplification products formed from FMDV serotype $O_{Taiwan}$ RNA using the P2Fwd-10 primer in combination with three reverse primers P33-4, LJS1 and LJS2 primers, respectively.

Figure 5:
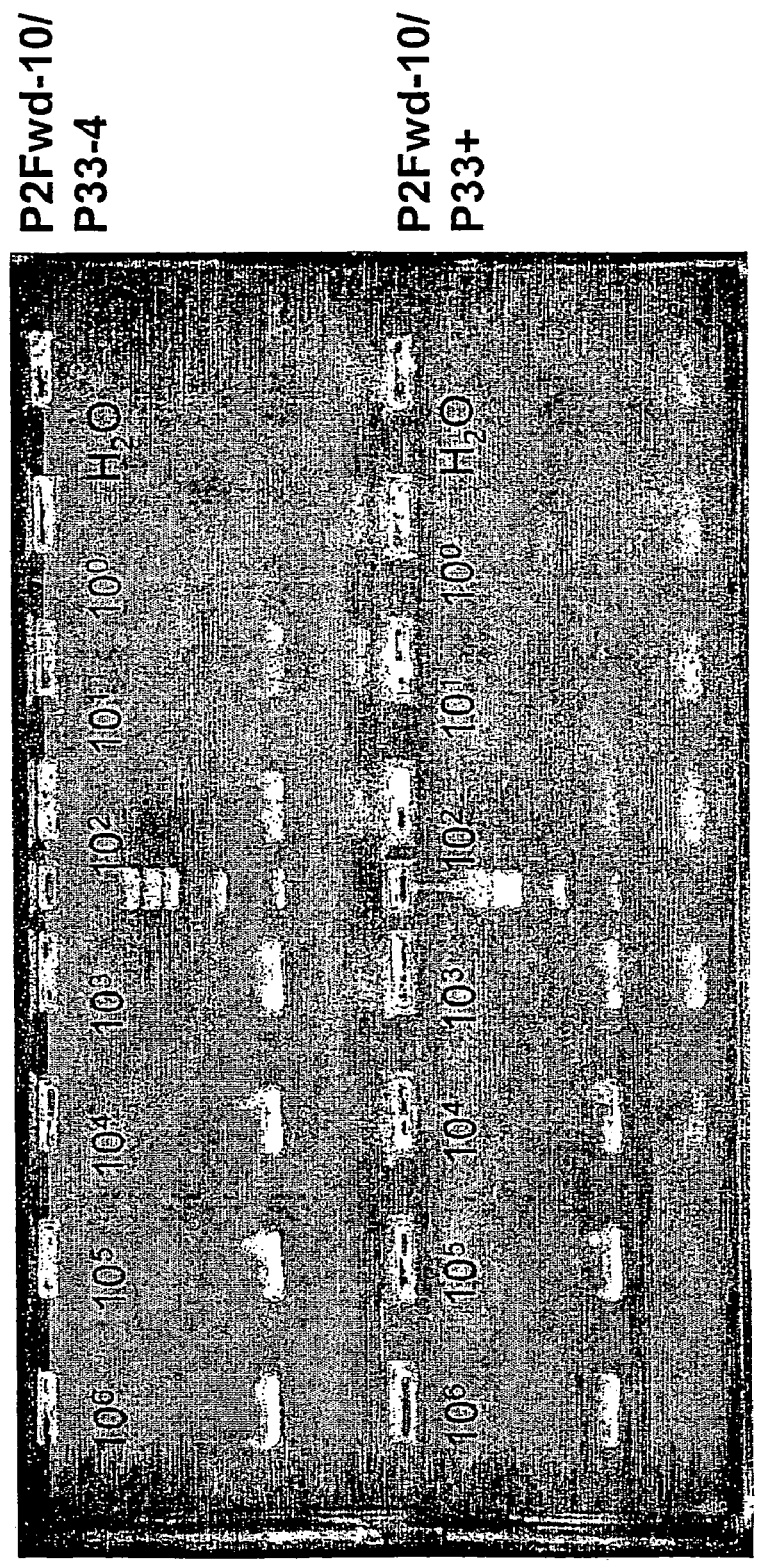

FIG. 5 is an agarose electrophoresis gel showing the RT-PCR amplification products formed from the synthetic FMD RNA using the P2Fwd-10 primer in combination with P33-4 or P33+ primers.

FIG. 6 shows the process of melting curve analysis in general. The change in fluorescence of the target DNA is captured during melting. Mathematical analysis of the negative of the change of the log of fluorescence divided by the change in temperature plotted against the temperature results in the graphical peak known as a melting curve.

The invention can be more fully understood from the following detailed description and the accompanying sequence listing, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-13 are linkers for construction of synthetic FMD DNA.

SEQ ID NO:14 and SEQ ID NO:15 encodes primers Amplicon 5' and Amplicon 3'.

SEQ ID NO:16 is the nucleotide sequence of a 5' Forward diagnostic primer, P2Fwd-10, which is derived from 3903-3929 bp of GenBank AF308157.

SEQ ID NO:17 is the nucleotide sequence of a 3' Reverse diagnostic primer, P33-4, which binds to 4086-4108 bp of GenBank AF308157.

SEQ ID NO:18 is the nucleotide sequence of a 3' Reverse diagnostic primer, P33+, which binds to 4083-4111 bp of GenBank AF308157.

SEQ ID NO:19 is the nucleotide sequence of a 3' Reverse diagnostic primer, LJS1, which binds to 4460-4489 bp of GenBank AF308157.

SEQ ID NO:20 is the nucleotide sequence of a 3' Reverse diagnostic primer, LJS2, which binds to 4317-4341 bp of GenBank AF308157.

SEQ ID NO:21 is the nucleotide sequence of the synthetic FMD target shown in FIG. 1.

DETAILED DESCRIPTION OF THE INVENTION

The disclosure of each reference set forth herein is incorporated by reference in its entirety.

Definitions

In this disclosure, a number of terms and abbreviations are used. The following definitions are provided.

"Polymerase chain reaction" is abbreviated PCR.

"Foot and Mouth Disease Virus" is abbreviated FMDV.

"Foot and Mouth Disease" is abbreviated FMD.

"Reverse transcription followed by polymerase chain reaction" is abbreviated RT-PCR.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "polynucleotide", "polynucleotide sequence", "nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more strands of cDNA, genomic DNA, synthetic DNA, or mixtures thereof.

The term "amplification product" refers to nucleic acid fragments produced during a primer-directed amplification reaction. Typical methods of primer-directed amplification include polymerase chain reaction (PCR), reverse transcription followed by PCR (RT-PCR), ligase chain reaction (LCR) or strand displacement amplification (SDA). If PCR methodology is selected, the replication composition may comprise the components for nucleic acid replication, for example: nucleotide triphosphates, two (or more) primers with appropriate sequences, DNA or RNA polymerase, buffers, solutes and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions may comprise, for example: a thermostable ligase (e.g., *T. aquaticus* ligase), two sets of adjacent oligonucleotides (wherein one member of each set is complementary to each of the target strands), Tris-HCl buffer, KCl, EDTA, NAND, dithiothreitol and salmon sperm DNA. See, for example, Tabor et al., *Proc. Acad. Sci. U.S.A.*, 82:1074-1078 (1985)). Additional methods of RNA replication such as replicative RNA system (Qβ-replicase) and DNA dependent RNA-polymerase promoter systems (T7 RNA polymerase) are also contemplated.

The term "reverse transcription followed by polymerase chain reaction", or "RT-PCR", refers to a sensitive technique for qualitative or quantitative analysis of gene expression, cloning, cDNA library construction, probe synthesis, and signal amplification in in situ hybridizations. The technique consists of two parts: synthesis of cDNA from RNA by reverse transcription (RT), and amplification of a specific cDNA by polymerase chain reaction (PCR). Reverse Transcriptase is an RNA-dependent DNA polymerase that catalyses the polymerization of nucleotides using template RNA, DNA, or RNA:DNA hybrids. It is preferred to utilize a total RNA isolation technique that yields RNA lacking significant amounts of genomic DNA contamination, since the subsequent PCR cannot discriminate between cDNA targets synthesized by reverse transcription and genomic DNA contamination.

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase.

The term "probe" refers to an oligonucleotide (synthetic or occurring naturally) that is complementary (though not necessarily fully complementary) to a polynucleotide of interest and forms a duplexed structure by hybridization with at least one strand of the polynucleotide of interest.

The term "replication inhibitor moiety" refers to any atom, molecule or chemical group that is attached to the 3' terminal hydroxyl group of an oligonucleotide that will block the initiation of chain extension for replication of a nucleic acid strand. Examples include, but are not limited to: 3'-deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide, or peptide nucleic acid units. The term "non-participatory" will refer to the lack of participation of a probe or primer in a reaction for the amplification of a nucleic acid molecule. Specifically a non-participatory probe or primer is one that will not serve as a substrate for, or be extended by, a DNA or RNA polymerase. A "non-participatory probe" is inherently incapable of being chain extended by a polymerase. It may or may not have a replication inhibitor moiety.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5× SSC, 0.5% SDS. Moderate stringency hybridization conditions correspond to a higher Tm, e.g., 40% formamide, with 5× or 6× SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one preferred embodiment the length for a hybridizable nucleic acid is at least about 10 nucleotides. More preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Recombinant DNA construct" refers to any gene that is not a native gene, comprising regulatory and coding sequences that are not found together in nature. Accordingly, a recombinant DNA construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or recombinant DNA constructs. A "transgene" is a gene that has been introduced into the genome by a transformation procedure.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), DNASTAR (DNASTAR, Inc., Madison, Wis.), and Vector NTi version 7.0. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual,* $2^{nd}$ ed., Cold Spring Harbor Laboratory: Cold Spring Harbor, N.Y. (1989) (hereinafter "Maniatis"); and by Ausubel, F. M. et al., *Current Protocols in Molecular Biology*, published by Greene Publishing Assoc. and Wiley-Interscience (1987).

The Foot and Mouth Disease Virus Genome

The FMDV genome (approximately 7-8 kB) consists of a single RNA positive strand encoding four structural proteins termed VP1, VP2, VP3, and VP4, and at least 10 non-structural proteins. The non-structural proteins are encoded within sections of the genome referred to as P2 and P3. These sections can be further divided into regions 2A, 2B, and 2C, and 3A, 3B, 3C, and 3D, respectively. Various combinations of these regions encode proteins involved in viral replication. The principal viral replicase gene is located in the region known as 3D, which is about 1.5 kB in size.

Although seven distinct serotypes of FMDV have been identified to date, variations within each serotype have also been identified. Portions of many of these better known and studied variations have been sequenced; additionally, the complete genome sequence is available for the several serotypes and variations. See for example:

1. Foot-and-mouth disease virus O genomic RNA, isolate O1Campos, complete genome (Accession No. AJ320488); Pereda, A. J., et al. Arch. Virol. 147 (11): 2225-2230 (2002);
2. Foot-and-mouth disease virus SAT 2, complete genome (Accession No. NC003992);
3. Foot-and-mouth disease virus C, complete genome (Accession No. NC002554); Baranowski, E., et al., J. Virol. 72 (8): 6362-6372 (1998);
4. Foot-and-mouth disease virus O strain China/1/99 (Tibet), complete genome (Accession No. AF506822);
5. Foot-and-mouth disease virus C strain C-S8 clone MARLS, complete genome (Accession No. AF274010); Baranowski, E., et al. (supra);
6. Foot-and-mouth disease virus O, complete genome (Accession No. AF308157); Beard, C. W. and Mason, P. W. *J. Virol.* 74 (2): 987-991 (2000)).

Sequence accession numbers are from the GenBank data base at National Center for Biotechnology Information, National Library of Medicine, Bldg. 38A, Room 8N-803, Bethesda, Md. 20894.

Identification of Diagnostic Region and Primer Design

The present invention includes a set of primers useful in a variety of assay formats for the highly sensitive detection of the Foot and Mouth Disease Virus (FMDV). As explained further herein, these primers may also be used as or in the design of hybridization probes.

The 2A/2B locus of the FMD genome was selected for primer design based on the universal homology observed when multiple of the seven different serotypes were aligned using Vector NTi alignment tools. Also, the 2A/2B regions are involved in viral replication. Thus, it was reasonable to predict that these gene sequences and subsequent proteins would be conserved among the FMD serotypes, making them attractive targets for a RT-PCR test.

Preferred primers used herein are those that have homology to specific regions of the 2A/2B locus (e.g., bp 3864-3917 and 3918-4379 of AF308157) of the FMD and include the forward or 5' primer as set forth in SEQ ID NO:16 and the three 3' reverse primers as set forth in SEQ ID NOs:17-18 and 20. One additional preferred primer is the 3' reverse primer as set forth in SEQ ID NO:19, which binds to the 2C region (e.g., bp 4380-5333 of AF308157) The location in the FMDV Serotype O from which each of SEQ ID NOs:16-20 is derived is shown below in Table 1.

TABLE 1

Primer sequences diagnostic for FMDV

| Primer | SEQ ID No. | Location in FMDV Serotype O (GenBank AF308157) |
|---|---|---|
| P2Fwd-10, Forward | 16 | 3903-3929 |
| P33-4, Reverse | 17 | 4086-4108 |
| P33+, Reverse | 18 | 4083-4111 |
| LJS1, Reverse | 19 | 4460-4489 |
| LJS2, Reverse | 20 | 4317-4341 |

These primers are broadly useful to detect FDMV infections across a plurality of serotypes and variations and in FMDV infections Assay Methods SEQ ID NOs:16-20 may be used in a variety of formats for the detection of FMDV. Most preferred are primer-directed amplification methods and nucleic acid hybridization methods.

These methods may be used to detect FMDV in a sample, e.g., from an animal, environmental or food source suspected of coming in contact with the FMDV. The sample and methods of collecting the sample may include, but are not limited to: swabs from oral and nasal cavities, body fluids (e.g., blood, blood serum, urine, fecal material, saliva, cerebrospinal fluid, lymph fluid, amniotic fluid, peritoneal fluid), tissues (e.g., muscle, skin) or bone samples. Additionally, air and soil samples may be used.

Primer-Directed Amplification Assay Methods

In one preferred embodiment, SEQ ID NOs:16-20 may be used as primers for use in primer-directed nucleic acid amplification for the detection of the presence of FMDV. A variety of primer-directed nucleic acid amplification methods are known in the art including thermal cycling methods (e.g., PCR, RT-PCR, and LCR), as well as isothermal methods and strand displacement amplification (SDA).

The preferred method is PCR, and more specifically RT-PCR for detection of FMDV. Preferred primer pairs are: (i) SEQ ID NOs:16 and 17; (ii) SEQ ID NOs:16 and 18; (iii) SEQ ID NOs:16 and 19; and (iv) SEQ ID NOs:16 and 20. Most preferred is the primer pair SEQ ID NOs:16 and 17.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well-known in the art (Thein and Wallace, "The use of oligonucleotide as specific hybridization probes in the Diagnosis of Genetic Disorders", In *Human Genetic Diseases: A Practical Approach*, K. E. Davis Ed., (1986) pp 33-50; IRL: Herndon, V A; and Rychlik, W. (1993) In White, B. A. (ed.), *Methods in Molecular Biology*, Vol. 15, pp 31-39, PCR Protocols: Current Methods and Applications. Humania: Totowa, N.J.).

Amplification Conditions

A skilled person will understand that generally acceptable RT-PCR conditions may be used for successfully detecting FMDV using the primers of the instant invention. Depending on the sample to be tested, complexity of the assay procedure and degree of sensitivity required, optimization of the RT-PCR conditions may be necessary to achieve optimal sensitivity and specificity.

In a preferred embodiment, RT-PCR is performed on a per test basis as follows (the source of the reagents is set forth in the Examples section, unless otherwise noted).

One reaction tube (i e., one test) contains 50 μL of the following:

1. 45 μL of the following:

| Reagent | Final Conc. (per 50 μL) |
|---|---|
| PCR Buffer II pH 8.3 | 1× |
| KCl | 50 mM |
| Tris-HCl | 10 mM |
| $MgCl_2$ | 2 mM |
| DNTP | 200 or 250 μm |
| Forward primer (e.g. P2Fwd-10) | 600 nM |
| Reverse primer (e.g. P33-4) | 2 μM |
| SYBR ® Green | 1× |
| FastTaq (or HotTaq) | 2.5 U |
| Multiscribe reverse transcriptase | 1.25 U |
| RNase Inhibitor | 20 U |
| BSA | 24 μG |
| DMSO | 3.90% |
| Water (to adjust to Final Conc. of the above) | |

2. 5 μL of the test sample.

Total=50 μL/test.

Another preferred embodiment involves the use of certain reagents in tableted form. One reaction tube (i.e., one test) contains 50 μL of the following:

I. One tablet containing:

| Reagent | Final Conc. (per 50 μL) |
|---|---|
| Carbowax* | 1.86 mM |
| Trehalose** | 360.5 mM |
| dNTP | 250 μM |
| Forward Primer (e.g. P2Fwd-10) | 720 nM |
| Reverse Primer (e.g. P33-4) | 2.4 μM |
| SYBR ® Green | 1× |
| FastTaq (or HotTaq) | 3 U |
| Multiscribe transcriptase | 1.5 U |
| BSA | 28.8 μG |

*from Sigma Aldrich, Catalog #P5413
**from Sigma Aldrich, Catalog #T9531

II. 45 μL of the following:

| Reagent | Final Conc. (per 50 μL) |
|---|---|
| PCR Buffer II pH 8.3 | 1× |
| KCl | 50 mM |
| Tris-HCl | 10 mM |
| $MgCl_2$ | 2 mM |
| RNase Inhibitor | 20 U |
| DMSO | 3.90% |
| Water (to adjust to Final Conc. of the above) | |

III. 5 μL of the test sample.

Total=50 μL/test.

Preferred RT-PCR cycling conditions are:

| | Temperature (° C.) | Time |
|---|---|---|
| Stage 1: | 50 | 10 min |
| Stage 2: | 95 | 6 min* |
| Stage 3 (35 cycles) | 95 | 15 sec |
| | 71 | 60 sec |
| Stage 4: | 71 | 5 min |

*preferably when FastStart is used; preferably 15 min when HotTaq is used.

Detection

Primer-directed amplification products can be analyzed using various methods.

Homogenous detection refers to a preferred method for the detection of amplification products where no separation (such as by gel electrophoresis) of amplification products from template or primers is necessary. Homogeneous detection is typically accomplished by measuring the level of fluorescence of the reaction mixture in the presence of a fluorescent dye.

In a preferred embodiment, DNA melting curve analysis is used to carry out homogenous detection, particularly with the BAX® System hardware and reagent tablets from Qualicon Inc. The details of the system are given in U.S. Pat. No. 6,312,930 and PCT Publication Nos. WO 97/11197 and WO 00/66777, each of which is hereby incorporated by reference in its entirety.

Melting curve analysis detects and quantifies double stranded nucleic acid molecule ("dsDNA" or "target") by monitoring the fluorescence of the target amplification product ("target amplicon") during each amplification cycle at selected time points.

As is well known to the skilled artisan, the two strands of a dsDNA separate or melt, when the temperature is higher than its melting temperature. Melting of a dsDNA molecule is a process, and under a given solution condition, melting starts at a temperature (designated $T_{MS}$ hereinafter), and completes at another temperature (designated $T_{ME}$ hereinafter). The familiar term, $T_m$, designates the temperature at which melting is 50% complete.

A typical PCR cycle involves a denaturing phase where the target dsDNA is melted, a primer annealing phase where the temperature optimal for the primers to bind to the now-single-stranded target, and a chain elongation phase (at a temperature $T_E$) where the temperature is optimal for DNA polymerase to function.

According to the present invention, $T_{MS}$ should be higher than $T_E$, and $T_{ME}$ should be lower (often substantially lower) than the temperature at which the DNA polymerase is heatinactivated. Melting characteristics are effected by the intrinsic properties of a given dsDNA molecule, such as deoxynucleotide composition and the length of the dsDNA.

Intercalating dyes will bind to double stranded DNA. The dye/dsDNA complex will fluoresce when exposed to the appropriate excitation wavelength of light, which is dye dependent, and the intensity of the fluorescence may be proportionate to concentration of the dsDNA. Methods taking advantage of the use of DNA intercalating dyes to detect and quantify dsDNA are known in the art. Many dyes are known and used in the art for these purposes. The instant methods also take advantage of such relationship.

An example of such dyes includes intercalating dyes. Examples of such dyes include, but are not limited to, SYBR Green-I®, ethidium bromide, propidium iodide, TOTO®-1 {Quinolinium, 1-1'-[1,3-propanediylbis [(dimethyliminio)-3,1-propanediyl]]bis[4-[(3-methyl-2(3H)-benzothiazolylidene) methyl]]-, tetraiodide}, and YoPro® {Quinolinium, 4-[(3-methyl-2(3H)-benzoxazolylidene)methyl]-1-[3-(trimethylammonio)propyl]-,diiodide}. Most preferred for the instant invention is a non-asymmetrical cyanide dye such as SYBR Green-I®, manufactured by Molecular Probes, Inc. (Eugene, Oreg.).

Melting curve analysis is achieved by monitoring the change in fluorescence while the temperature is increased. When the temperature reaches the $T_{MS}$ specific for the target amplicon, the dsDNA begins to denature. When the dsDNA denatures, the intercalating dye dissociates from the DNA and fluorescence decreases. Mathematical analysis of the negative of the change of the log of fluorescence divided by the change in temperature plotted against the temperature results in the graphical peak known as a melting curve (See FIG. 6, which illustrates melting curve analysis in general).

The data transformation process shown in FIG. 6 involves the following:

1. Interpolate data to get evenly spaced data points
2. Take a log of the fluorescence (F)
3. Smooth log F
4. Calculate −d(log F)/dT
5. Reduce data to 11-13 data points spaced one degree apart (depending on the target organism).

A positive detection for FMDV results in the appearance of a melting curve peak as follows:

| Amplicon from Primer Pair: | Melting Peak (° C.) |
|---|---|
| SEQ ID NOs: 16 and 17 | 83-87 |
| SEQ ID NOs: 16 and 18 | Not Yet Determined |
| SEQ ID NOs: 16 and 19 | Not Yet Determined |
| SEQ ID NOs: 16 and 20 | Not Yet Determined |

It is believed that the melting point range of 83-87° C. exists due to the variation of GC/AT content in each serotype and the variation among topotypes of each serotype.

The instant homogenous detection method can be used to detect and quantify target dsDNAs, from which the presence and level of target organisms can be determined. This method is very specific and sensitive. The fewest number of target dsDNA detectable is between one and 10 under typical reaction conditions and volumes.

Homogenous detection may be employed to carry out "real-time" primer-directed nucleic acid amplifications, using primer pairs of the instant invention (e.g., "real-time" PCR and "real-time" RT-PCR). Preferred "real-time" methods are set forth in U.S. Pat. Nos. 6,171,785 and 5,994,056, each of which is hereby incorporated by reference in its entirety.

Another detection method is the 5' nuclease detection method, as set forth in U.S. Pat. Nos. 5,804,375, 5,538,848, 5,487,972, and 5,210,015, each of which is hereby incorporated by reference in its entirety.

A variety of other PCR detection methods are known in the art including standard non-denaturing gel electrophoresis (e.g., acrylamide or agarose), denaturing gradient gel electrophoresis, and temperature gradient gel electrophoresis. Standard non-denaturing gel electrophoresis is a simple and quick method of PCR detection, but may not be suitable for all applications.

Denaturing Gradient Gel Electrophoresis (DGGE) is a separation method that detects differences in the denaturing behavior of small DNA fragments (200-700 bp). The principle of the separation is based on both fragment length and nucleotide sequence. In fragments that are the same length, a difference as little as one base pair can be detected. This is in contrast to non-denaturing gel electrophoresis, where DNA fragments are separated only by size. This limitation of non-denaturing gel electrophoresis results because the difference in charge density between DNA molecules is near neutral and plays little role in their separation. As the size of the DNA fragment increases, its velocity through the gel decreases.

DGGE is primarily used to separate DNA fragments of the same size based on their denaturing profiles and sequence. Using DGGE, two strands of a DNA molecule separate, or melt, when heat or a chemical denaturant is applied. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking". Consequently, a DNA molecule may have several melting domains with each of their individual characteristic denaturing conditions determined by their nucleotide sequence. DGGE exploits the fact that otherwise identical DNA molecules having the same length and DNA sequence, with the exception of only one nucleotide within a specific denaturing domain, will denature at different temperatures or Tm. Thus, when the double-stranded (ds) DNA fragment is electrophoresed through a gradient of increasing chemical denaturant it begins to denature and undergoes both a conformational and mobility change. The dsDNA fragment will travel faster than a denatured single-stranded (ss) DNA fragment, since the branched structure of the single-stranded moiety of the molecule becomes entangled in the gel matrix. As, the denaturing environment increases, the ds DNA fragment will completely dissociate and mobility of the molecule through the gel is retarded at the denaturant concentration at which the particular low denaturing domains of the DNA strand dissociate. In practice, the electrophoresis is conducted at a constant temperature (around 60° C.) and chemical denaturants are used at concentrations that will result in 100% of the DNA molecules being denatured (i.e., 40% formamide and 7M urea). This variable denaturing gradient is created using a gradient maker, such that the composition of each DGGE gel gradually changes from 0% denaturant up to 100% denaturant. Of course, gradients containing a reduced range of denaturant (e.g., 35% to 60%) may also be poured for increased separation of DNA.

The principle used in DGGE can also be applied to a second method that uses a temperature gradient instead of a chemical denaturant gradient. This method is known as Temperature Gradient Gel Electrophoresis (TGGE). This method makes use of a temperature gradient to induce the conformational change of dsDNA to ssDNA to separate fragments of equal size with different sequences. As in DGGE, DNA fragments with different nucleotide sequences will become immobile at different positions in the gel. Variations in primer design can be used to advantage in increasing the usefulness of DGGE for characterization and identification of the PCR products. These methods and principles of using primer design variations are described in PCR Technology Principles and Applications, Henry A. Erlich Ed., M. Stockton Press, NY, pages 71 to 88 (1988).

Instrumentation

According to a preferred embodiment, the BAX® System (DuPont Qualicon, Wilmington, Del.) and melting curve analysis are used.

Reagents and Kits

Any suitable nucleic acid replication composition ("replication composition") in any format can be used.

A typical replication composition for PCR or RT-PCR amplification may comprise, for example, dATP, dCTP, dGTP, dTTP, and a suitable polymerase and reverse transcriptase, in conjunction with target specific primers, and various cofactors modifying enzyme/primer specificity and activity.

A preferred replication composition comprises (a) at least one pair of PCR primers selected from the group consisting of (i) SEQ ID NOs:16 and 17, (ii) SEQ ID NOs:16 and 18, (iii) SEQ ID NOs:16 and 19; and (iv) SEQ ID NOs:16 and 20; (b) thermostable DNA polymerase; and (c) reverse transcriptase.

If the replication composition is in liquid form, suitable buffers known in the art may be used (Sambrook, J. et al. 1989, Molecular Cloning: A Laboratory Manual, Second Edition, Cold Spring Harbor Laboratory Press).

Alternatively, if the replication composition is contained in a tablet form, then typical tabletization reagents may be included such as stabilizers and binding agents. Preferred tabletization technology is set forth in U.S. Pat. Nos. 4,762,857 and 4,678,812, each of which is hereby incorporated by reference in its entirety.

A preferred kit for detection of FMDV comprises (a) at least one pair of PCR primers selected from the group consisting of (i) SEQ ID NOs:16 and 17, (ii) SEQ ID NOs:16 and 18, (iii) SEQ ID NOs:16 and 19;

and (iv) SEQ ID NOs:16 and 20; (b) thermostable DNA polymerase; and (c) reverse transcriptase.

A preferred tablet comprises (a) at least one pair of PCR primers selected from the group consisting of (i) SEQ ID NOs:16 and 17, (ii) SEQ ID NOs:16 and 18, (iii) SEQ ID NOs:16 and 19; and (iv) SEQ ID NOs:16 and 20; (b) thermostable DNA polymerase; and (c) reverse transcriptase. Even more preferably, a kit for detection of FMDV comprises the foregoing preferred tablet.

In another preferred embodiment, a replication composition contains an internal positive control. The advantages of an internal positive control contained within a PCR reaction have been previously described (U.S. Pat. No. 6,312,930 and PCT Application No. WO 97/11197, each of which is hereby incorporated by reference in its entirety, and include: (i) the control may be amplified using a single primer; (ii) the amount of the control amplification product is independent of any target DNA or RNA contained in the sample; (iii) the control DNA can be tableted with other amplification reagents for ease of use and high degree of reproducibility in both manual and automated test procedures; (iv) the control can be used with homogeneous detection, i.e., without separation of product DNA from reactants; and (v) the internal control has a melting profile that is distinct from other potential amplification products in the reaction Control DNA will be of appropriate size and base composition to permit amplification in a primer-directed amplification reaction. The control DNA sequence may be obtained from the FMDV genome, or from another source, but must be reproducibly amplified under the same conditions that permit the amplification of the target amplification product.

The control reaction is useful to validate the amplification reaction. Amplification of the control DNA occurs within the same reaction tube as the sample that is being tested, and therefore indicates a successful amplification reaction when samples are target negative, i.e. no target amplification product is produced. In order to achieve significant validation of the amplification reaction a suitable number of copies of the control DNA or RNA must be included in each amplification reaction.

In some instances it may be useful to include an additional negative control replication composition. The negative control replication composition will contain the same reagents as the replication composition but without the polymerase. The primary function of such a control is to monitor spurious background fluorescence in a homogeneous format when the method employs a fluorescent means of detection.

Nucleic Acid Hybridization Methods

Probes particularly useful in nucleic acid hybridization methods are any of SEQ ID NOs: 16-20 or sequences derived therefrom.

The basic components of a nucleic acid hybridization test include a probe, a sample suspected of containing FMDV, and a specific hybridization method. Probes are single stranded nucleic acid sequences which are complementary to the nucleic acid sequences to be detected. Probes are "hybridizable" to the nucleic acid sequence to be detected. Typically the probe length can vary from as few as 5 bases to the full length of the FMDV diagnostic sequence and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base. A probe may be composed of either RNA or DNA. The form of the nucleic acid probe may be a marked single stranded molecule of just one polarity or a marked single stranded molecule having both polarities present. The form of the probe, like its length, will be determined by the type of hybridization test to be done.

The sample may or may not contain the FMDV. The sample may take a variety of forms, however will generally be extracted from an animal, environmental or food source suspected of coming in contact with the FMDV. The sample and methods of collecting the sample may include, but are not limited to: swabs from oral and nasal cavities, body fluids (e.g., blood, blood serum, urine, fecal material, saliva, cerebrospinal fluid, lymph fluid, amniotic fluid, peritoneal fluid), tissues (e.g., muscle, skin) or bone samples. Additionally, air and soil samples may be used.

The FMDV RNA may be detected directly but most preferably, the sample nucleic acid must be made available to contact the probe before any hybridization of probe and target molecule can occur. Thus the organism's DNA must be free from the cell and placed under the proper conditions before hybridization can occur. Methods of in solution hybridization necessitate the purification of the DNA in order to be able to obtain hybridization of the sample DNA with the probe. This has meant that utilization of the in solution method for detection of target sequences in a sample requires that the nucleic acids of the sample must first be purified to eliminate protein, lipids, and other cell components, and then contacted with the probe under hybridization conditions. Methods for the purification of the sample nucleic acid are common and well known in the art (Maniatis, supra).

Similarly, hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed.

In one preferred embodiment, hybridization assays may be conducted directly on cell lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to DNA at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Alternatively, one can purify the sample nucleic acids prior to probe hybridization. A variety of methods are known to one of skill in the art (e.g., phenol-chloroform extraction, Iso-Quick extraction (MicroProbe Corp., Bothell, Wash.), and others). Pre-hybridization purification is particularly useful for standard filter hybridization assays. Furthermore, purification facilitates measures to increase the assay sensitivity by incorporating in vitro RNA amplification methods such as self-sustained sequence replication (see for example Fahy et al., In *PCR Methods and Applications*, Cold Spring Harbor Laboratory: Cold Spring Harbor, N.Y. (1991), pp. 25-33) or reverse transcriptase PCR (Kawasaki, In *PCR Protocols: A Guide to Methods and Applications*, M. A. Innis et al., Eds., (1990), pp. 21-27).

Once the RNA or DNA is released, it can be detected by any of a variety of methods. However, the most useful embodiments have at least some characteristics of speed, convenience, sensitivity, and specificity.

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents which include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the DNA sequence.

The sandwich assay may be encompassed in an assay kit. This kit would include a first component for the collection of samples from an animal suspected of having contracted the FMDV and buffers for the disbursement and lysis of the sample. A second component would include media in either dry or liquid form for the hybridization of target and probe polynucleotides, as well as for the removal of undesirable and nonduplexed forms by washing. A third component includes a solid support (dipstck) upon which is fixed (or to which is conjugated) unlabeled nucleic acid probe(s) that is (are) complementary to a part of the FMDV genome. A fourth component would contain labeled probe that is complementary to a second and different region of the same DNA strand to which the immobilized, unlabeled nucleic acid probe of the third component is hybridized.

In another preferred embodiment, SEQ ID NOs:16-20 or derivations thereof may be used as 3' blocked detection probes in either a homogeneous or heterogeneous assay format. For example, a probe generated from these sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic or cDNA isolated from a sample suspected of harboring the FMDV is amplified by standard primer-directed amplification protocols in the presence of an excess of the 3' blocked detection probe to produce amplification products. Because the probe is 3' blocked, it does not participate or interfere with the amplification of the target. After the final amplification cycle, the detection probe anneals to the relevant portion of the amplified DNA and the annealed complex is then captured on a support through the reactive ligand.

In some instances it is desirable to incorporate a ligand labeled dNTP, with the label probe in the replication composition to facilitate immobilization of the RT-PCR reaction product on a support and then detection of the immobilized product by means of the labeled probe reagent. For example a biotin, digoxigenin or digoxin labeled dNTP could be added to RT-PCR reaction composition. The biotin or digoxin incorporated in the RT-PCR product could then be immobilized respectively on to a strepavidin, anti-dixogin or antidigoxigenin antibody support. The immobilized RT-PCR product could then be detected by the presence of the probe label.

Probes of the instant invention may be designed in several alternate forms. The 3' end of the probe is blocked from participating in a primer extension reaction by the attachment of a replication inhibiting moiety. Typical replication inhibitor moieties will include, but are not limited to: dideoxynucleotides, 3-deoxynucleotide, a sequence of mismatched nucleosides or nucleotides, 3' phosphate groups and chemical agents. Cordycepin (3' deoxyadenosine) is preferred.

The replication inhibitor is covalently attached to the 3' hydroxy group of the 3' terminal nucleotide of the non-participatory probe during chemical synthesis, using standard cyanoethyl phosphoramidite chemistry. This process uses solid phase synthesis chemistry in which the 3' end is covalently attached to an insoluble support (controlled pore glass, or "CPG") while the newly synthesized chain grows on the 5' terminus. 3-deoxyribonucleotides are the preferred replication inhibitors. Cordycepin (3-deoxyadenosine) is most preferred. Since the cordycepin will be attached to the 3' terminal end of the probe, the synthesis is initiated from a cordycepin covalently attached to CPG, 5-dimethoxytrityl-N-benzoyl-3-deoxyadenosine (cordycepin), 2-succinoyl-long chain alkylamino-CPG (Glen Research, Sterling, Va.). The dimethoxytrityl group is removed and the initiation of the chain synthesis starts at the deprotected 5' hydroxyl group of the solid phase cordycepin. After the synthesis is complete, the oligonucleotide probe is cleaved off the solid support leaving a free 2' hydroxyl group on the 3'-terminally attached cordycepin. Other reagents can also be attached to the 3' terminus during the synthesis of the non-participatory probe to serve as replication inhibitors. These include, but are not limited to: other 3-deoxyribonucleotides, biotin, dinitrophenol, fluorescein, and digoxigenin. Each of these reagents are also derivatized on CPG supports (Glen Research; Clonetech Laboratories, Palo Alto, Calif.).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); by T. J. Silhavy, M. L. Bennan, and L. W. Enquist, Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology: Washington, D.C. (1994)) or by Thomas D. Brock in *Biotechnology: A Textbook of Industrial Microbiology*, 2nd ed., Sinauer Associates: Sunderland, Mass. (1989).

Enzymes and reagents used herein were purchased from the following vendors:

Applied Biosystems, Foster City, Calif.: AmpliTaq (Catalog #N808-0160), Multiscribe (Catalog #4311235); RNase Inhibitor (Catalog #N808-0119); Buffer II (1 mM Tris-HCl pH 8.3, 5 mM KCl) (Catalog #N808-0190); MgCl$_2$ (Catalog #N808-0190)

New England Biology, Beverly, Mass.: EcoRI (Catalog #R0101L); Not I (Catalog #R0189L); T4 DNA Ligase (Catalog #M0202L); T4 polynucleotide kinase (Catalog #M0201L )

Bionexus Inc., Oakland, Calif.: Hot Taq (Catalog #D1002HB);

Sigma Genosys, The Woodlands, Tex.: Oligonucleotides;

Qiagen, Valencia, Calif.: Rnase-Free Dnase Set (Catalog #79254);

Invitrogen Life Technologies, Carlsbad, Calif.: Ampicillian (Catalog #11593-019); Carbenicillin (Catalog #10177-012); 2% Agarose E-gels (Cat #G6018-02); Luria Broth (LB) media (Catalog #10855-021); Triazol LS Reagent (Catalog #10296-028); Diethylprocarbonate (DEPC) water (Catalog #10813-012)

Sigma-Aldrich, St. Louis, Mo.: Bovin Serum Albumin (BSA) (Catalog #A3294); Dimethyl Sulfoxide (DMSO) (Catalog #D8418)

Roche Diagnostics, Indianapolis, Ind.: FastStart Taq (Catalog #2032937); dNTP (Catalog #1814362)

Additionally, test kits and reagents were purchased from the following vendors: pCR4-TOPO vector (Invitrogen Life Technologies, Catalog #45-0030); Qiagen QlAquick PCR Purification Kit (Qiagen, Catalog #28104); Qiagen Rneasy Mini Kit (Catalog #74106); Qiagen QlAprep Spin Mini Prep Kit (Catalog # 27106); RNA Transcription kit (Stratagene, Catalog #200340, Cedar Creek, Tex.); and TOPO TA Cloning Kit Dual Promoter (Invitrogen Life Technologies, Catalog #45-0640).

All oligonucleotide primers and linkers were synthesized by Sigma Genosys Company, The Woodlands, Tex. Polymerase chain reactions and RNA quantitations were performed using a PTC-225 Peltier Thermal Cycler (M J Research Waltham, Mass.) and GeneQuant pro (Catalog #80-2110-98; Amersham Pharmacia Biotech, Cambridge, England).

Analysis and construction of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. In any case where GCG program parameters were not prompted for, in these or any other GCG program, default values were used.

The meaning of abbreviations is as follows: "sec" means second(s), "min" means minute(s), "hr" means hour(s), "d" means day(s), "µL" means microliter(s), "mL" means milliliter(s), "L" means liter(s), "µM" means micromolar, "mM" means millimolar, "M" means molar, "mmol" means millimole(s), "µmol" mean micromole(s), "ng" means nanogram(s), "µg" means microgram(s), "mg" means milligram(s), "g" means gram(s), "mU" means milliunit(s), and "U" means unit(s).

Construction of a Synthetic RNA Target (3800-4290 bp of FMDV serotype O)

A synthetic piece of a foot and mouth virus (FMDV) RNA serotype O (GenBank Accession Number AF308157; Beard, C. W. and Mason, P. W., *J. Virology* 74(2): 987-991 (2000)) was constructed from base 3800 to 4290. The synthetic FMD target was constructed using 13 total DNA linkers (SEQ ID NOs: 1-13) comprising both top and bottom strands (FIG. 1).

NotI and EcoRI sites were added to the sequence of synthetic DNA target to facilitate directional cloning of the construct behind the T7 promoter in the pCR4-TOPO vector.

Linkers were kinased, ligated and PCR amplified using primers Amplicon 5' and Amplicon 3' (SEQ ID NOs:14 and 15, respectively) in accordance to published protocols with modifications (Maniatis, supra, pp 5.68-5.69, 1.68-1.69, 14.2-14.19).

Construction of a Synthetic DNA (3800-4290 bp of FMDV serotype O)

To construct the synthetic FMD DNA, linkers (SEQ ID NOs: 1-13) were diluted with DEPC treated water to 25 pmoles/µL. Linkers (25 pmoles of each) were combined in one tube. To this tube 10 µL of 10×T4 Kinase buffer, 100 Units of T4 Kinase, 1 mM ATP and DEPC water to 100 µL final volume was added. The reaction was incubated for 30 min at 37° C. The kinased linkers mix was heated at 95° C. for 20 min in a heat block to inactivate the kinase and melt all the linkers. After the 20 min the heat block was turned off and allowed to cool, thereby facilitating proper linker annealing.

Once the linkers cooled to room temperature, the ligation reaction was set-up as follows: in a total volume of 100 µl, 85 µL of the kinased-annealed linkers, 10 µL of 10×ligase buffer, and 50 Units of Ligase were added. The reaction proceeded for 30 min at room temperature or overnight at 14° C. Following ligation, the product was amplified by PCR to add restriction sites (if necessary) and to bulk up the quantity of product available for subsequent cloning. In a 50 µL reaction 1 µL of annealed, ligated linkers were added to a PCR tube with 1× Buffer II, 3.5 mM MgCl$_2$, 250 µM dNTP, 2.5 Units Taq, and 20 pmol of forward and reverse primers. Thermocycling conditions were: 20 cycles of 95° C. (30 sec), 55° C. (30 sec), 72° C. (30 sec), followed by a final extension at 72° C. (5 min) and a hold at 4° C. The PCR product was cleaned-up with Qiagen QIAquick PCR Purification Kit. The PCR product was subsequently digested with NotI/EcoRI and cloned into pCR4-TOPO vector cut with NotI/EcoRI.

Cloning of the Synthetic Target

The PCR product produced above was cloned using topoisomerase-cloning technology (TOPO) developed by Invitrogen. The TOPO TA Cloning Dual Promoter Kit was used for the initial cloning of the synthetic FMD piece. Putative clones were transformed into competent E. coli provided by the Invitrogen kit (Top10F'). E. coli harboring vectors (with or without inserts) were selected for on LB media containing 50-100 µg/ml ampicillian or carbenicillian for vector selection. Positive clones, containing the insert, were determined by growing up individual colonies in 4 ml of LB broth supplemented with 100 µg/ml ampicillian overnight at 37° C. with 230 rpm shaking. Mini-prep DNA was prepared using a QIAprep Spin Mini Prep Kit. Clones were analyzed by restriction endonuclease digest or PCR for correctness, as determined by insert size.

Figure 2:
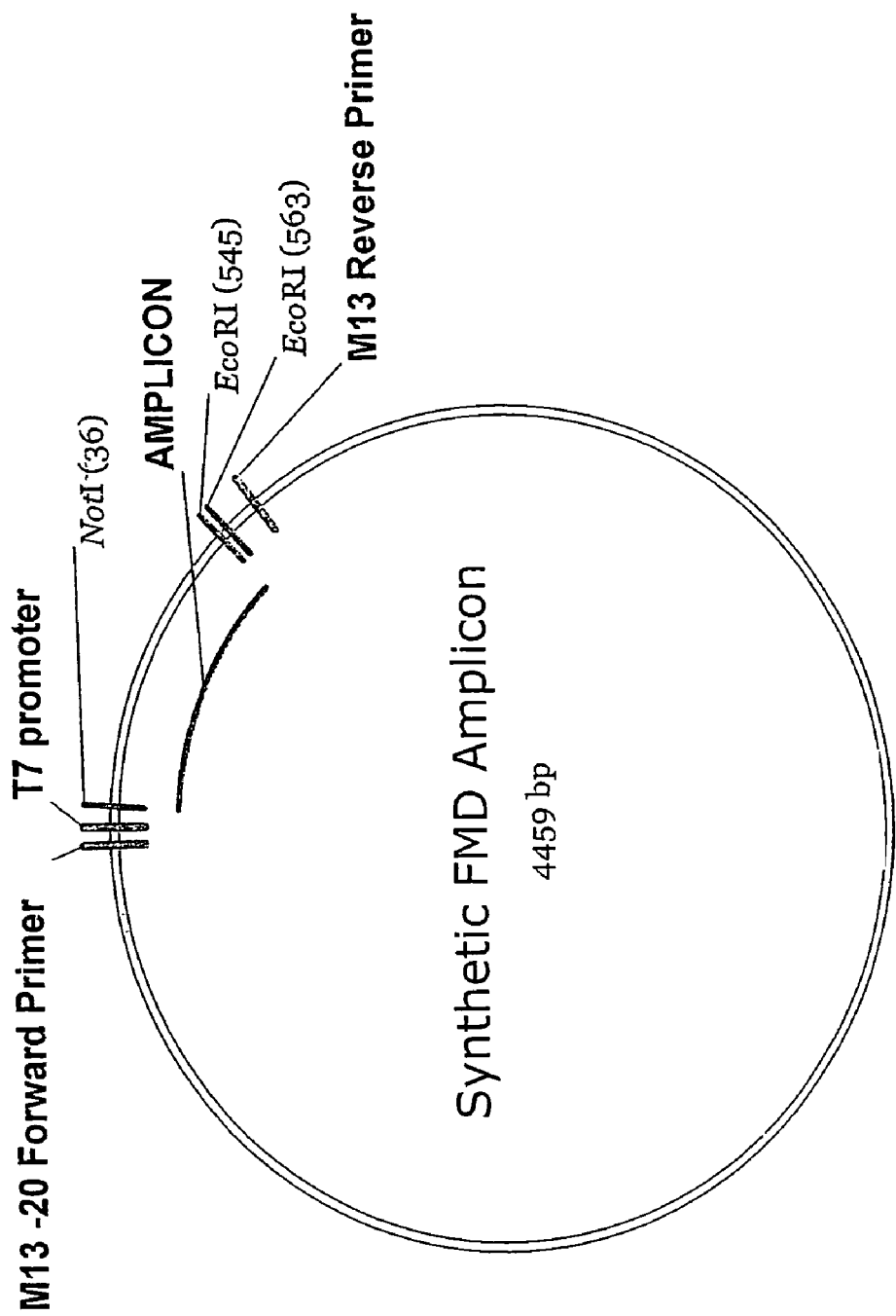
FIG. 2 is a plasmid map showing the synthetic FMD DNA construct.

The final cloning step entailed removal of the synthetic FMD fragment by enzymatically removing the insert from the TOPO TA Cloning vector using Not I and EcoRI. These restriction sites (NotI and EcoRI) were added to the ends of the synthetic FMD fragment to facilitate directional cloning of the 5-prime end behind a prokaryotic T7 promoter of the pCR4-TOPO vector. The T7 promoter facilitates RNA transcription of the synthetic FMD fragment. The final synthetic FMD construct (FIG. 2), was sequenced using the M13 forward and reverse primers located on either side of the T7 synthetic FMD portion of the clone; specifically, the M13-20 Forward primer is located at 4437-4452 bp, while the M13 Reverse primer is located at 629-645 bp. The Synthetic FMD DNA is located from 36-536 bp and the T7 promoter is located at the 5'-end of the synthetic FMD DNA from 1-20 bp.

Sequencing was conducted using fluorescent BigDye terminator chemistry (Applied Biosystems, Foster City, Calif. 94404). The synthetic FMD DNA construct had an identical sequence to the original serotype O sequence from base 3800 to 4290.

FMD virus is positive strand RNA virus. A positive stand RNA copy of the synthetic FMD DNA molecule prepared above was synthesized by copying the FMD DNA (FIG. 1) using a T7 polymerase and the Stratagene RNA transcription kit. The RNA transcripts product was then purified and used as a surrogate FMD target molecule for reverse transcription polymerase chain reaction (RT-PCR). In this process, the synthetic FMD construct was first linearized with EcoRI. The digested DNA was passed through a Qiagen PCR clean-up column, thus facilitating removal of restriction endonucleases and salts. The T7 polymerase included in Stratagene's RNA Transcription kit was used to synthesize RNA from the T7 promoter located adjacent to the FMD synthetic construct. Synthetic RNA was purified using Qiagen's Mini-RNA clean-up protocol including the optional 15-minute DNAse step. RNA was eluded in DEPC treated water. Molecules of synthetic FMD RNA per micro liter were determined spectrophotometrically (GeneQuant pro) and log base ten serial dilutions were routinely generated for use in RT-PCR reactions.

Example 1

Demonstration of an RT-PCR Assay for Detection of FMD using Synthetic FMDV RNA

A single step RT-PCR assay for the FMD target sequence was performed on the synthetic FMD RNA target using the following reagents and conditions. Each reaction was performed in a 50 µl total reaction volume.

First, a pre-reaction mix was prepared for each of the four primer pairs, as follows. The forward primer P2Fwd-10 (SEQ ID NO:16) and reverse primer (SEQ ID NO:17, 18, 19, or 20) were dissolved in water and added respectively to the reaction solution at concentrations of respectively at 600 nM and 2 µM per test. Buffer II (1×) was added to comprise a final concentration of 1 mM Tris-HCl pH 8.3, 5 mM KCl and 3.5 mM MgCl$_2$. Nucleotides were used at 250 µM per test. BSA was used at a final concentration of 0.6 mM per test. SYBR Green (Catalog # 517695#S7564; Molecular Probes, Eugene, Oreg.) was added in DMSO to a final dilution of 1:40,000. Enzymes were used at 2.5 Units Taq polymerase, 20 Units Rnase Inhibitor, and 1.25 Units Multiscribe reverse transcriptase per 50 µl test. The reaction solution (45 µl) was then stored on ice.

Samples containing synthetic RNA dissolved in water were added at 5 µl per reaction. The tube(s) were sealed and then thermal cycled using the following conditions:

50° C. 10 minutes (RT step);
95° C. 15 minutes (Taq activation step);
95° C. 15 second (denature step);
71° C. 1 minute (anneal and extend step);
Repeat denature and anneal steps 35 times;
71° C. 10 minutes;
4° C. hold.

The RT-PCR reaction products were then analyzed using agarose gel electrophoresis using 2% E-gels. Following electrophoresis the gels were then viewed to determine the presence or absence of a correct size RT-PCR product (224 bp product of SEQ ID NOs:16 and 17; P2Fwd-10/LJS1 (SEQ ID NOs:16 and 19) and P2Fwd-10/LJS2 (SEQ ID NOs:16 and 20) primer sets form larger products (554 bp and 400 bp, respectively)).

RT-PCR reactions were performed with each of the four primer pairs (i.e., SEQ ID NO:16 and each of SEQ ID NOs: 17-20) using serial log dilutions of the synthetic FMD RNA. Sample concentrations ranged from $10^7$ copies to $10^1$ copies/reaction.

FIG. 3A shows results obtained using the primer pair P2Fwd-10 and P33-4 (SEQ ID NO:16 and 17). Reactions were carried out and performed as described above. Specifically, the RT-PCR product is shown using serial log dilutions of the synthetic FMD target RNA from $10^7$ copies to $10^1$ copies/test. As can be seen in FIG. 3A, the primers sensitivity allows detection of 10 copies of target RNA. The center lane contains molecular weight markers (Invitrogen low molecular weight standard).

Example 2

RT-PCR Test Response using FMD Viral Serotypes with P2Fwd-10 and P33-4 Primer Set This example illustrates the RT-PCR assay response to representative strains of all seven FMD viral serotypes and demonstrates that all seven serotypes can be detected.

Virus samples, each containing representative strains of all seven serotypes of FMD (O, A, C, Asia1, Sat 1, Sat 2 and Sat 3) were cultivated from field samples using in vitro tissue culture cell lines by Gordon Ward, USDA, APHIS, Greenport, N.Y. Plaque forming unit (PFU) and tissue culture infectious dose ($TCID_{50}$) determinations on the cultures established the viral titers for each sample (as described in *Virology, A Practical Approach*. B W J Mahy, Ed.; IRL: Oxford and Washington D.C., 1985; Chapter 2, pp 25-35).

FMD viral RNA from the samples was isolated using the Triazol LS extraction chemistry and method as outlined by the manufacturer (Invitrogen Life Technologies, Catalog #10296-028). The recovered RNA was then reconstituted in water. Seven log dilutions were made of each FMD serotype RNA extraction.

RT-PCR reactions were performed on each of the diluted RNA serotype samples using the conditions and procedure described in Example 1. FIG. 3B is a photograph of an agarose electrophoresis gel showing the typical RT-PCR product formed using samples containing a 10,000-fold dilution of the original viral RNA extracts. In this experiment, 5 μl of water was used a Negative, no-virus sample. P2Fwd-10 and P33-4 primers (SEQ ID NOs:16 and 17) were used for RT-PCR with a representative strain for each of the seven FMD viral serotypes at $10^2$ viral RNA copies/test. Viral RNA copies were determined from the viral PFU/ml and $TCID_{50}$/ml culture values. The center lane contains molecular weight markers (Invitrogen low molecular weight standard). As shown in FIG. 3B, the correct size RT-PCR product was formed with each FMD viral serotype demonstrating that the test universally detects RNA from all seven serotypes.

Example 3

RT-PCR Detection Sensitivity to FMD Serotypes

The limit of test detection for each of the seven FMD viral serotypes tested using the RT-PCR assay with the P2Fwd-10/P33-4 primers (SEQ ID NOs:16 and 17) is shown in Table 2. In this example, serial dilutions of the RNA extracted from the FMD viral cultures described above were tested using the RT-PCR assay as described in Example 1. Columns 2 and 4 of the table show the FMD virus concentrations of the original tissue cultures in $TCDI_{50}$/ml and PFU/ml units. Columns 3 and 4 show the lowest detectable dose of viral RNA detected by the RT-PCR assay in $TCDI_{50}$/ml and PFU/ml units. As shown below in Table 2, all seven serotypes of FMD are detectable at levels<10 $TCID_{50}$/ml and<0.5 PFU/ml respectively.

TABLE 2

RT-PCR Test Sensitivity Using P2Fwd-10-/P33-4 Primer Set

| FMD Serotype | Virus Conc. $TCID_{50}$/ml | RT-PCR Sensitivity $TCID_{50}$/ml | Virus Conc. PFU/ml | RT-PCR Sensitivity PFU/ml |
|---|---|---|---|---|
| O | 8.0E + 06 | 0.8 | 7.8E + 06 | 0.02 |
| A | 1.0E+06 | 1 | 1.2E+06 | 0.03 |
| C | 3.0E+06 | 3 | 3.3E+06 | 0.05 |
| Asia 1 | 8.0E+06 | 8 | 8.0E+06 | 0.2 |
| Sat1 | 2.0E+06 | 2 | 2.3E+06 | 0.06 |
| Sat2 | 3.0E+06 | 3 | 3.0E+06 | 0.08 |
| Sat3 | 4.0E+06 | 4 | 3.7E+06 | 0.09 |

Example 4

RT-PCR Assay Using P2Fwd-10 Forward Primer and Three Different Reverse 3' Primers Forming Larger Products Example 4 illustrates the utility of additional primer combinations to produce RT-PCR test products of different sizes. In this example, FMD serotype O Taiwan RNA substrate was detected using the same RT-PCR conditions described in Example 1. However, in this example, the P2Fwd-10 forward primer (SEQ ID NO: 16) was used in combination with three different reverse primers: P33-4 (SEQ ID NO:17), LJS1 (SEQ ID NO:19), or LJS2 (SEQ ID NO:20).

The advantages of the P2Fwd-10/LJS1 and P2Fwd-10/LJS2 primer sets are that they form a larger product (554 bp and 400 bp, respectively) compared to P2Fwd-10/P33-4 (224 bp). Also, the products of P2Fwd-10/LJS1 and P2Fwd-10/LJS2 primer sets can act as a substrate for half-nested PCR using the P2Fwd-10/P33-4 primer set.

Seven 10-fold serial dilutions were prepared of FMD serotype O RNA extracted in Example 2. These were tested using the above primer combinations and the RT-PCR reagent concentrations and thermal cycling conditions in Example 1. Following thermal cycling, agarose gel electrophoresis was run on the reaction products and imaged. FIG. 4 illustrates the reaction products formed in response to RT-PCR reactions using the three primer sets. Specifically, FIG. 4 is a composite picture of three agarose gels showing the RT-PCR products formed to serotype O $_{Taiwan}$ RNA using the P2Fwd-10 primer in combination with P33-4, LJS1 and LJS2 primers. The RNA concentration in PFU/ml used per reaction is listed above each lane. The reverse primer type and observed product size are listed to the left of the gel picture. The fourth lane contains the molecular weight markers (Invitrogen low molecular weight standard).

According to the results, each of the primer sets produced the correct product size as determined by the FMD serotype O gene sequence. LJS1 and LJS2 primers exhibited test sensitivity down to 10² and 10¹ copies, respectively, and P33-4 was sensitive down to 10⁻¹ PFU/ml.

Example 5

RT-PCR Test Response using Various Combinations of 5' Forward and 3' Reverse Primers This example illustrates the utility of additional primer combinations for RT-PCR FMD detection. In this example, serial dilutions of the synthetic FMD RNA were tested from 10⁷ to 10⁰ copies per reaction. A negative control was used in addition to the diluted RNA to determine the response of the test in the absence of viral RNA. The RNA was amplified with either the P2Fwd-10/P33-4 (SEQ ID NOs: 16 and 17) or P2Fwd-10/P33+ (SEQ ID NOs: 16 and 18) primer sets. RT-PCR reactions concentration and thermal cycling conditions were the same as described in Example 1. FIG. 5 shows the gel analysis of the reaction products. The RNA concentration in copies used per reaction is listed above each lane. The fifth lane contains the molecular weight markers (Invitrogen low molecular weight) standard). Both primer sets amplify amplicon RNA. The P2Fwd-10/P33-4 primer set was sensitive to sample concentrations down to 10⁰ copies/reaction and the P2Fwd-10/P33+ primer set was sensitive down to down to 10² copies/reaction.

What is claimed is:

1. A method for detecting the presence of FMDV in a sample, the method comprising:
   (a) performing RT-PCR amplification of the sample using at least one primer pair selected from the group consisting of:
      (i) SEQ ID NOs:16 and 17,
      (ii) SEQ ID NOs:16 and 18,
      (iii) SEQ ID NOs:16 and 19, and
      (iv) SEQ ID NOs:16 and 20,
      to produce an RT-PCR amplification result; and
   (b) examining the RT-PCR amplification result of step (a) to detect for an amplification product of the primer pair, whereby a positive detection of the amplification product indicates the presence of FMDV in the sample.

2. The method of claim 1, wherein in step (b) a melting curve analysis is used to detect for an amplification product.

3. The method of claim 1, further comprising a step of extracting RNA from the sample prior to said step (a).

4. A primer for use in PCR amplification for detection of FMDV consisting essentially of SEQ ID NO:16, SEQ ID NO:17, SEQ ID NO:18, SEQ ID NO:19, or SEQ ID NO:20.

5. A kit for detection of FMDV, comprising:
   (a) at least one primer pair selected from the group consisting of:
      (i) SEQ ID NOs:16 and 17,
      (ii) SEQ ID NOs:16 and 18,
      (iii) SEQ ID NOs:16 and 19, and
      (iv) SEQ ID NOs:16 and 20;
   (b) reverse transcriptase; and
   (c) thermostable DNA polymerase.

6. A replication composition for use in performance of RT-PCR, comprising:
   (a) at least one primer pair selected from the group consisting of:
      (i) SEQ ID NOs:16 and 17,
      (ii) SEQ ID NOs:16 and 18,
      (iii) SEQ ID NOs:16 and 19, and
      (iv) SEQ ID NOs:16 and 20;
   (b) reverse transcriptase; and
   (c) thermostable DNA polymerase.

7. A tablet comprising the replication composition of claim 6.

8. A kit for detection of FMDV in a sample, comprising the tablet of claim 6.

* * * * *

SEQUENCE LISTING

<160> NUMBER OF SEQ ID NOS: 21

<210> SEQ ID NO 1
<211> LENGTH: 86
<212> TYPE: DNA
<213> ORGANISM: Artificial Sequence
<220> FEATURE:
<223> OTHER INFORMATION: Linker for construction of synthetic FMD DNA

<400> SEQUENCE: 1
ggccgcgccc ccggccactt ttggccattc acccgagcga agctagacac aaacaaaaga      60
ttgtggcacc ggtgaaacag cttttg                                           86

<210> SEQ ID NO 2
<211> LENGTH: 84
<212> TYPE: DNA
<213> ORGANISM: Artificial Sequence
<220> FEATURE:
<223> OTHER INFORMATION: Linker for construction of synthetic FMD DNA

<400> SEQUENCE: 2
agctttgacc tgctcaagtt ggcaggggac gtcgagtcca accctgggcc tttcttcttc      60
tctgacgtta ggtcaaattt ttcc                                             84

<210> SEQ ID NO 3
<211> LENGTH: 87
<212> TYPE: DNA
<213> ORGANISM: Artificial Sequence
<220> FEATURE:
<223> OTHER INFORMATION: Linker for construction of synthetic FMD DNA

<400> SEQUENCE: 3
aagttggttg aaaccatcaa ccagatgcag gaggacatgt caacaaaaca cggacccgac      60
tttaaccggt tggtgtctgc atttgag                                          87

<210> SEQ ID NO 4
<211> LENGTH: 89
<212> TYPE: DNA
<213> ORGANISM: Artificial Sequence
<220> FEATURE:
<223> OTHER INFORMATION: Linker for construction of synthetic FMD DNA

<400> SEQUENCE: 4
gaactggcca ccggagtgaa ggctatcagg accggtctcg atgaggccaa acctggtac       60 aagctcatca agctcttgag ccgcctgtc                                        89

<210> SEQ ID NO 5

-continued

```
<211> LENGTH: 85
<212> TYPE: DNA
<213> ORGANISM: Artificial Sequence
<220> FEATURE:
<223> OTHER INFORMATION: Linker for construction of synthetic FMD DNA

<400> SEQUENCE: 5
atgtatggcc gctgtagcag cacggtcaaa ggacccagtc cttgtggcca tcatgctggc     60
tgacaccggc cttgagattc tggac                                           85

<210> SEQ ID NO 6
<211> LENGTH: 78
<212> TYPE: DNA
<213> ORGANISM: Artificial Sequence
<220> FEATURE:
<223> OTHER INFORMATION: Linker for construction of synthetic FMD DNA

<400> SEQUENCE: 6
agtacctttg tcgtgaagaa gatctccgac tcgctctcca gtctctttca cgtaccggcc     60
cccgtcttca gtttcggg                                                   78

<210> SEQ ID NO 7
<211> LENGTH: 55
<212> TYPE: DNA
<213> ORGANISM: Artificial Sequence
<220> FEATURE:
<223> OTHER INFORMATION: Linker for construction of synthetic FMD DNA

<400> SEQUENCE: 7
cttttgtttg tgtctagctt cgctcgggtg aatggccaaa agtggccggg ggcgc           55

<210> SEQ ID NO 8
<211> LENGTH: 59
<212> TYPE: DNA
<213> ORGANISM: Artificial Sequence
<220> FEATURE:
<223> OTHER INFORMATION: Linker for construction of synthetic FMD DNA

<400> SEQUENCE: 8
acgtcccctg ccaacttgag caggtcaaag ctcaaaagct gtttcaccgg tgccacaat       59

<210> SEQ ID NO 9
<211> LENGTH: 85
<212> TYPE: DNA
<213> ORGANISM: Artificial Sequence
<220> FEATURE:
<223> OTHER INFORMATION: Linker for construction of synthetic FMD DNA

<400> SEQUENCE: 9
ctcctgcatc tggttgatgg tttcaaccaa cttggaaaaa tttgacctaa cgtcagagaa     60
gaagaaaggc ccagggttgg actcg                                           85

<210> SEQ ID NO 10
<211> LENGTH: 86
<212> TYPE: DNA
<213> ORGANISM: Artificial Sequence
<220> FEATURE:
<223> OTHER INFORMATION: Linker for construction of synthetic FMD DNA

<400> SEQUENCE: 10
gtcctgatag ccttcactcc ggtggccagt tcctcaaatg cagacaccaa ccggttaaag     60
tcgggtccgt gttttgttga catgtc                                          86
```

<210> SEQ ID NO 11
<211> LENGTH: 83
<212> TYPE: DNA
<213> ORGANISM: Artificial Sequence
<220> FEATURE:
<223> OTHER INFORMATION: Linker for construction of synthetic FMD DNA

<400> SEQUENCE: 11
accgtgctgc tacagcggcc atacatgaca ggcggctcaa gagcttgatg agcttgtacc 60
agggtttggc ctcatcgaga ccg 83

<210> SEQ ID NO 12
<211> LENGTH: 85
<212> TYPE: DNA
<213> ORGANISM: Artificial Sequence
<220> FEATURE:
<223> OTHER INFORMATION: Linker for construction of synthetic FMD DNA

<400> SEQUENCE: 12
gagatcttct tcacgacaaa ggtactgtcc agaatctcaa ggccggtgtc agccagcatg 60
atggccacaa ggactgggtc ctttg 85

<210> SEQ ID NO 13
<211> LENGTH: 54
<212> TYPE: DNA
<213> ORGANISM: Artificial Sequence
<220> FEATURE:
<223> OTHER INFORMATION: Linker for construction of synthetic FMD DNA

<400> SEQUENCE: 13
aattcccgaa actgaagacg gggccggta cgtgaaagag actggagagc gagc 54

<210> SEQ ID NO 14
<211> LENGTH: 32
<212> TYPE: DNA
<213> ORGANISM: Artificial Sequence
<220> FEATURE:
<223> OTHER INFORMATION: Primer Amplicon 5'

<400> SEQUENCE: 14
gcggccgcgc ccccggccac ttttggccat tc 32

<210> SEQ ID NO 15
<211> LENGTH: 33
<212> TYPE: DNA
<213> ORGANISM: Artificial Sequence
<220> FEATURE:
<223> OTHER INFORMATION: Primer Amplicon 3'

<400> SEQUENCE: 15
gaattcccga aactgaagac gggggccggt acg 33

<210> SEQ ID NO 16
<211> LENGTH: 27
<212> TYPE: DNA
<213> ORGANISM: Artificial Sequence
<220> FEATURE:
<223> OTHER INFORMATION: Primer P2-Fwd2, which binds to 3903-3929 bp of
GenBank AF308157

<400> SEQUENCE: 16
gagtccaacc ctgggccctt cttcttc 27

<210> SEQ ID NO 17
<211> LENGTH: 23

-continued

<212> TYPE: DNA
<213> ORGANISM: Artificial Sequence
<220> FEATURE:
<223> OTHER INFORMATION: Primer P33-4, which binds to 4086-4108 bp of GenBank AF308157

<400> SEQUENCE: 17
atgagcttgt accagggttt ggc 23

<210> SEQ ID NO 18
<211> LENGTH: 29
<212> TYPE: DNA
<213> ORGANISM: Artificial Sequence
<220> FEATURE:
<223> OTHER INFORMATION: Primer P33+, which binds to 4083-4111 bp of GenBank AF308157

<400> SEQUENCE: 18
ttgatgagct tgtaccaggg tttggcctc 29

<210> SEQ ID NO 19
<211> LENGTH: 30
<212> TYPE: DNA
<213> ORGANISM: Artificial Sequence
<220> FEATURE:
<223> OTHER INFORMATION: Primer LJS1, which binds to 4460-4489 bp of GenBank AF308157

<400> SEQUENCE: 19
tctgaggcga tccatgcctt aatccagtcg 30

<210> SEQ ID NO 20
<211> LENGTH: 25
<212> TYPE: DNA
<213> ORGANISM: Artificial Sequence
<220> FEATURE:
<223> OTHER INFORMATION: Primer LJS2, which binds to 4317-4341 bp of GenBank AF308157

<400> SEQUENCE: 20
ggaagaaact cgaggcgacc ttgac 25

<210> SEQ ID NO 21
<211> LENGTH: 516
<212> TYPE: DNA
<213> ORGANISM: Artificial sequence
<220> FEATURE:
<223> OTHER INFORMATION: Synthetic FMD target

<400> SEQUENCE: 21
gcggccgcgc ccccggccac ttttggccat tcacccgagc gaagctagac acaaacaaaa 60
gattgtggca ccggtgaaac agcttttgag ctttgacctg ctcaagttgg caggggacgt 120
cgagtccaac cctgggcctt tcttcttctc tgacgttagg tcaaattttt ccaagttggt 180
tgaaaccatc aaccagatgc aggaggacat gtcaacaaaa cacggacccg actttaaccg 240
gttggtgtct gcatttgagg aactggccac cggagtgaag gctatcagga ccggtctcga 300
tgaggccaaa ccctggtaca agctcatcaa gctcttgagc cgcctgtcat gtatggccgc 360
tgtagcagca cggtcaaagg acccagtcct tgtggccatc atgctggctg acaccggcct 420
tgagattctg gacagtacct ttgtcgtgaa gaagatctcc gactcgctct ccagtctctt 480
tcacgtaccg gcccccgtct tcagtttcgg gaattc 516